United States Patent [19]
Bienkowski

[11] Patent Number: 5,831,055
[45] Date of Patent: Nov. 3, 1998

[54] DNA ENCODING A NOVEL KIDNEY ATP-DEPENDENT POTASSIUM CHANNELS

[75] Inventor: Michael J. Bienkowski, Portage, Mich.

[73] Assignee: Pharmacia & Upjohn Company, Kalamazoo, Mich.

[21] Appl. No.: 709,923

[22] Filed: Sep. 9, 1996

Related U.S. Application Data

[60] Provisional application No. 60/003,839, Sep. 15, 1995.

[51] Int. Cl.$^6$ ............................ C12N 15/12; C12N 15/09; C12N 15/10; C12N 15/11
[52] U.S. Cl. ...................... 536/23.5; 435/69.1; 435/252.3
[58] Field of Search ............................... 435/325, 252.3, 435/254.11, 69.1; 536/23.5; 530/350

[56] References Cited

U.S. PATENT DOCUMENTS 5,492,625  2/1996  Jan et al. ................................ 435/352

FOREIGN PATENT DOCUMENTS

92/02634  2/1992  WIPO .
92/02639  2/1992  WIPO .
94/19464  9/1994  WIPO .

OTHER PUBLICATIONS

Hillier et al. ye33c06.r1 Homo sapiens cDNA clone 119530 5′ similar to SP:IRKA RAT P35560 ATP–sensitive inward rectifier potassium channel ROMK1. EST–STS Accession No. T94029, Mar. 24, 1995.
Bond, C. T., et al., *Receptors and Channels*, 2, pp. 183–191 (1994).
Takumi, T., et al., *J. Biol. Chem.*, 270, pp. 16339–16346 (1995).
Bredt, D. S., et al., *Proc. Natl. Acad. Sci.*, 92, pp. 6753–6757 (1995).
Ho, K., et al., *Nature*, 362, pp. 31–38 (1993).
Chandy, K., et al., *Science*, 247, pp. 973–975 (1990).
Lazdunski, M., *Cardiovascular Drugs and Therapy*, 6, pp. 313–319 (1992).
Shuck, M. E., et al., *J. Biol. Chem.*, 269, (39) pp. 24261–24270 (1994).
Inagaki, N., et al., *J. Biol. Chem.*, 270, pp. 5691–5694 (1995).
Doupnik, C. A., et al., *Current Opinion in Neurobiology*, 5, pp. 268–277 (1995).
Sakura, H., et al., *FEBS Lett.*, 367, pp. 193–197 (1995).
Kubo, Y., et al., *Nature*, 362, pp. 127–133 (1993).
Dascal, N., et al., *Proc. Natl. Acad. Sci. USA*, 90, pp. 10235–10239 (1993).
Morishige, K–I., et al., *FEBS Let.*, 336, pp. 375–380 (1993).
Ashen, M. D., et al., *Am. J. Physiol.*, 268, pp. H506–H511 (1995).
Koyama, H., et al., *FEBS Let.*, 341, pp. 303–307 (1994).
Wible, B. A., et al., *Circ. Res.*, 76, pp. 343–350 (1995).
Raab–Graham, K. F., et al., *Neuroreport*, 5, pp. 2501–2505 (1994).
Morishige, K–I., et al., *FEBS Let.*, 346, pp. 251–256 (1994).
Perier, F., et al., *Proc. Natl. Acad. Sci. USA*, 91, pp. 6240–6244 (1994).
Makhina, E. N., et al., *J. Biol. Chem.*, 269, pp. 20468–20474 (1994).
Tang, W., et al., *FEBS Let.*, 348, pp. 239–243 (1994).
Falk, T., et al., *FEBS Let.*, 367, pp. 127–131 (1995).
Kubo, Y., et al., *Nature*, 364, pp. 802–806 (1993).
Lesage, F., et al., *FEBS Let.*, 353, pp. 37–42 (1994).
Bond, C. T., et al., *FEBS Let.*, 367, pp. 61–66 (1995).
Tsaur, M–L., et al., *Diabetes*, 44, pp. 592–596 (1995).
Ashford, M. L. J., et al., *Nature*, 370, pp. 456–459 (1994).
Krapivinsky, G., et al., *Nature*, 374, pp. 135–141 (1995).
Duprat, F., et al., *Biochem. Biophys. Res. Comm.*, 212, pp. 657–663 (1995).
Shuck, M. E., et al., *J. Biol. Chem.*, 269, pp. 24261–24270 (1994).
George et al. (1988) Macromolecular Sequencing and Synthesis (Ed. by D.H. Schlesinger) Alan R. Liss, Inc., New York, pp. 127–149, 1988.
Reeck et al. (1987) Cell 50:667, Aug. 1987.

*Primary Examiner*—Stephen Walsh
*Assistant Examiner*—Michael Pak
*Attorney, Agent, or Firm*—Thomas A. Wootton

[57] ABSTRACT

The present invention comprises human DNA compositions, including cDNA clones, with full sequences, called, KIRK-2 and KIRK-3, encoding proteins that confer potassium channel activity to membranes or recipient cell lines. The DNA compositions include structural genes coding for the potassium channel proteins, expression and replication plasmids or vectors containing the structural genes and host cells expressing those genes. Methods of screening compounds for potassium channel modulating activity are also described.

1 Claim, 8 Drawing Sheets

DNA ENCODING A NOVEL KIDNEY ATP-DEPENDENT POTASSIUM CHANNELS

CROSS-REFERENCE TO RELATED APPLICATIONS

This application claims the benefit of U.S. provisional application Ser. No. 60/003,839 filed 15 Sep. 1995, under 35 USC §119(e)(i).

FIELD OF THE INVENTION

The present invention comprises human DNA compositions encoding proteins that confer potassium channel activity to membranes of recipient cell lines. The DNA compositions include structural genes coding for the potassium channel proteins, expression and replication plasmids or vectors containing the structural genes and host cells expressing those genes. Methods of screening compounds for potassium channel modulating activity are also described.

INFORMATION DISCLOSURE

Bond, C. T., Pessia, M., Xia, X-M., Lagrutta, A., Kavanaugh, M. P. and Adelman, J. P. "Cloning and expression of a family of inward rectifier potassium channels" *Receptors and Channels* 2: 183–191 (1994). Descriptions of a rat BIRK clone.

Takumi, T., Ishii, T., Horio, Y., Morishige, K-I., Takahashi, N., Yamada, M., Yamashita, T., Kiyama, H., Sohmiya, K., Nakanishi, S. and Kurachi, Y. "A novel ATP-dependent inward rectifier potassium channel expressed predominantly in glial cells" *J. Biol. Chem.* 270: 16339–16346 (1995). Descriptions of a rat BIRK clone.

Bredt, D. S., Wang, T-L., Cohen, N. A., Guggino, W. B. and Snyder, S. H. "Cloning and expression of two brain-specific inwardly rectifying potassium channels" *Proc. Natl. Acad. Sci. USA* 92: 6753–6757 (1995). Descriptions of a rat BIRK clone.

Bienkowski and Groppi, WO 94/19464, PCT/US94/01210, published 1 Sep. 1994. "Human DNA sequence encoding a kidney ATP-dependent potassium channel."

Ho, K., et. al. "Cloning and expression of an inwardly rectifying ATP-regulated potassium channel." *Nature* (4 Mar. 1993) Vol. 362 pp. 31–38. Describes the gene that encodes an ATP-regulated potassium channel protein from the inner stripe of outer medulla of rat kidneys.

Chandy, K., et. al., WO 92/02634, PCT/US91/05168, published 20 Feb. 1992. Describes the gene product known as MK3, a voltage dependent, type n potassium channel protein in T lymphocytes.

Chandy, K., et. al., "A Family of Three Mouse Potassium Channel Genes with Intronless Coding Regions." *Science* (23 Feb. 1990) Vol. 247, pp. 973–975

Harpold, M., and Brust P., W092/02639, PCT/US91/05625, published 20 Feb. 1992. Transcription assays that identify compounds that modulate the activity of cell surface proteins. Cells that contains DNA that encode reporter genes, transcriptional control elements and heterologous cell surface proteins that may be potassium ion channels.

Luzdunski, M., "Potassium Channels: Structure-Function Relationships, Diversity, and Pharmacology," *Cardiovascular Drugs and Therapy*, (1992) Vol. 6, pp. 312–319. General description and information concerning potassium channels.

References listed above are incorporated by reference.

BACKGROUND

Ionic channels of cell membranes are the basic sites where ionic fluxes take place. The modern era of the study of drug-channel interactions began when voltage clamp techniques were used to demonstrate the block of Sodium, ($Na^+$), and potassium, ($K^+$), channels of squid axons caused by procaine and cocaine. Narahashi, Ann Neurology (1984); 16(suppl): S39–S51.

This invention concerns potassium channels. Pharmacological and biophysical studies have revealed multiple subtypes for membrane ion channels that form potassium selective pores in the plasma membrane of many mammalian cells. Comparison of the pharmacological and electrophysiological properties of these potassium channels has given rise to an operational definition for grouping the various subtypes based largely on their gating properties.

Voltage-gated potassium channels sense changes in membrane potential and pass potassium ions in response to this alteration in the cell membrane potential. Ligand-gated potassium channels are regulated by small molecular weight effectors which include calcium, sodium, ATP or fatty acids (particularly arachidonic acid). Lazdunski, Cardiovascular Drugs and Therapy (1992) Vol. 6 pp. 313–319. Although these channel proteins share the common property that they selectively move potassium ions, their distinct biophysical, biochemical and pharmacological properties suggests that they are different gene products encoded by distinct genes.

The ATP-Sensitive, or ATP-gated, potassium channel is an important class of channels that links the bioenergetic situation of the cell to its electrical excitability. The channel is blocked by high intracellular ATP concentrations and it opens when ATP decreases. Lazdunski (1992). Although ATP-gated potassium channels were originally described in cardiac tissue; Noma, A. Nature (1983) Vol. 305 pp. 147–148, they have subsequently been described in pancreatic β-cells; Cook et. al., Nature (1984) Vol. 311 pp. 271–273, vascular smooth muscle; Nelson, M. T. et. al., Am. J. Physiol. (1990) Vol. 259 pp. C3–C18 and in the thick ascending limb of the kidney; Wang, W. et. al. Am. J. Physiol. (1990) Vol. 258, pp. F244–F-253.

The expression cloning of the ROMK[1], IRK[2] and G-protein regulated KGA[3] potassium channels has defined a new genetic class of potassium channels that can be regarded as simplified versions of the voltage-gated potassium channels. All of these potassium channel polypeptides share a homologous H-5 region that is believed to form a part of the K-selective pore. In contrast to the predicted structure of the voltage-gated K channels which contain six transmembrane domains and relatively small cytoplasmic domains, these three K channels are predicted to contain only two transmembrane domains which flank the H-5 segment and relatively large COOH-terminal cytoplasmic domains. The discovery of these cDNA sequences has facilitated the isolation and characterization other members of this family of K channels that currently includes 11 distinct members. Classification of these DNA sequences based on homology reveals 3 distinct subfamilies in which the ROMK, IRK-1 and KGA/GIRK channels represent the charter members. The ROMK subfamily contains two members in addition to ROMK. The closest genetic relative to ROMK, originally referred to as BIRK 10[4], has been independently cloned from rat brain [BIRK1 or $K_{AB}$-2][5,6]. A more distantly related K channel that may actually define a new sub-family distinct from ROMK, referred to as $uK_{ATP}$-1, has been cloned from rat pancreatic islets[7]. The IRK family contains 4 distinct members including IRK-1[2,8,9], IRK-2[10–12], IRK-3[13–17] and BIRK-9[5]. Finally, the GIRK family contains 4 members including GIRK-1[3,18], GIRK-2 (also referred to as $K_{ATP}$-2)[19–22], GIRK-3[19] and GIRK-4 [also referred to as cardiac $K_{ATP}$-1 and CIR][23,24]. Although our knowledge regarding the relationships between these cloned channels and their native counterparts is incomplete, there appear to be common functional features that support this genetic classification. All of these channels form inward rectifier K channels when expressed in heterologous systems. The IRK family all form K channels that show strong $Mg^{2+}$-dependent inward rectification while all of the GIRK family members are regulated by G-proteins[19] and are likely to form heteromultimers that have electrophysiological signatures that are distinct from the individual polypeptides[24,25]. Finally, the members of the ROMK family are regulated by $ATP^{(1,5,7)}$ suggesting that these polypeptides may form the core pore-forming subunit of the $K_{ATP}$ channel.

We have previously reported the cloning and characterization of multiple isoforms of the human ROMK channel from kidney that are formed by alternative splicing of a common gene[26]. To extend our understanding of the expression of other members of the ROMK family in the kidney, we have used the BIRK-10 cDNA cloned from rat brain as a probe to clone the human homolog from a kidney cDNA library.

REFERENCES CITED IN THE BACKGROUND

1. Ho, K., Nichols, C. G., Lederer, W. J., Lytton, J., Vassilev, P. M., Kanazirska, M. V. and Hebert, S. C. "Cloning and expression of an inwardly rectifying ATP-regulated potassium channel" *Nature* 362: 31–38 (1993).

2. Kubo, Y., Baldwin, T. J., Jan, Y. N. and Jan, L. Y. "Primary structure and functional expression of a mouse inward rectifier potassium channel" *Nature* 362: 127–133 (1993).

3. Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A. and Davidson, N. "Atrial G-protein-activated $K^+$ channel: Expression cloning and molecular properties" *Proc. Natl. Acad. Sci. USA* 90: 10235–10239 (1993).

4. Bond, C. T., Pessia, M., Xia, X-M., Lagrutta, A., Kavanaugh, M. P. and Adelman, J. P. "Cloning and expression of a family of inward rectifier potassium channels" *Receptors and Channels* 2: 183–191 (1994).

5. Takumi, T., Ishii, T., Horio, Y., Morishige, K-I., Takahashi, N., Yamada, M., Yamashita, T., Kiyama, H., Sohmiya, K., Nakanishi, S. and Kurachi, Y. "A novel ATP-dependent inward rectifier potassium channel expressed predominantly in glial cells" *J. Biol. Chem.* 270: 16339–16346 (1995).

6. Bredt, D. S., Wang, T-L., Cohen, N. A., Guggino, W. B. and Snyder, S. H. "Cloning and expression of two brain-specific inwardly rectifying potassium channels" *Proc. Natl. Acad. Sci. USA* 92: 6753–6757 (1995).

7. Inagaki, N., Tsuura, Y., Namba, N., Masuda, K, Gonoi, T., Horie, M., Seino, Y., Mizuta, M. and Seino, S. "Cloning and functional characterization of a novel $K_{ATP}$-sensitive potassium channel ubiquitously expressed in rat tissues including pancreatic islets, pituitary, skeletal muscle and heart" *J. Biol. Chem.* 270: 5691–5694 (1995).

8. Morishige, K-I., Takahashi, N., Findlay, I., Koyama, H., Zanelli, J. S., Peterson, C., Jenkins, N. A., Copeland, N. G., Mori, N. and Kurachi, Y. "Molecular cloning, functional expression and localization of an inward rectifier potassium channel in the mouse brain" *FEBS Let.* 336: 375–380 (1993).

9. Ashen, M. D., O'Rourke, B., Kiuge, K. A., Johns, D. C, and Tomaselli, G. F. "Inward rectifier $K^+$ channel from human heart and brain: cloning and stable expression in a human cell line" *Am. J. Physiol.* 268: (Heart Circ. Physiol.) H506–H511 (1995).

10. Koyama, H., Morishge, K-I., Takahashi, N., Zanelli, J. S., Fass, D. N. and Kurachi, Y. "Molecular cloning, functional expression of a novel inward rectifier potassium channel in the rat brain" *FEBS Let.* 341: 303–307 (1994).

11. Wible, B. A., Biasi, M., Majumder, K., Taglialatela, M. and Brown, A. M. "Cloning and functional expression of an inwardly rectifying $K^+$ channel from human atrium" *Circ. Res.* 76: 343–350 (1995).

12. Raab-Graham, K. F., Radeke, C. M. and Vanderberg, C. A. "Molecular cloning and expression of a human heart inward rectifier potassium channel" *Neuroreport.* 5: 2501–2505 (1994).

13. Morishe, K-I., Takahashi, N., Jahangir, A., Yamada, M., Koyama, H., Zanelli, J. S. and Kurachi, Y. "Molecular cloning and functional expression of a novel brain-specific inward rectifier potassium channel" *FEBS Let.* 346: 251–256 (1994).

14. Perier, F., Radeke, C. M. and Vanderberg, C. A. "Primary strucutre and characterization of a small conductance inwardly rectifying potassium channel from human hippocampus" *Proc. Natl. Acad. Sci. USA* 91: 6240–6244 (1994).

15. Makhina, E. N., Kelly, A. J., Lopatin, A. N., Mercer, R. W. and Nichols, C. G. "Cloning and expression of a novel brain inward rectifier potassium channel" *J. Biol. Chem.* 269: 20468–20474 (1994).

16. Tang, W. and Yang, X-C. "Cloning of a novel human brain inward rectifier potassium channel and its functional expression in Xenopus oocytes" *FEBS Let.* 348: 239–243 (1994).

17. Falk, T., Meyerhof, W., Corrette, B. J., Schafer, J., Bauer, C. K., Schwarz, J. and Richter, D. "Cloning, functional expression and mRNA distribution of an inwardly rectifying potassium channel protein" *FEBS Let.* 367: 127–131 (1995).

18. Kubo, Y., Reuveny, E., Slesinger, P. A., Jan Y. N. and Jan, L. Y. "Primary structure and functional expression of a rat G-protein-coupled muscarinic potassium channel" *Nature* 364: 802–806 (1993).

19. Lesage, F., Duprat, F., Fink, M., Guillemare, E., Coppola, T., Lazdunski, M. and Hugnot, J-P. "Cloning provides evidence for a family of inward rectifier and G-protein coupled $K^+$ channels in the brain" *FEBS Let.* 353: 37–42 (1994).

20. Bond, C. T., Ammala, C., Ashfield, R., Blair, T. A., Gribble, F., Khan, R. N., Lee, K., Proks, P., Rowe, I. C. M., Sakura, H., Ashford, M. J., Adelman, J. P. and Ashcroft, F. M. "Cloning and functional expression of the cDNA encoding an inwardly rectifying potassium channel expressed in pancreatic β-cells and in the brain" *FEBS Let.* 367: 61–66 (1995).

21. Sakura, H., Bond, C., Warren-Perry, M., Horsley, S., Kearney, L., Tucker, S., Adelman, J. P., Turner, R. and Ashcroft, F. M. "Characterization and variation of a human inwardly rectifying K-channel gene (KCNJ6): a putative ATP-sensitive K-channel subunit" *FEBS Let.* 367: 193–197 (1995).

22. Tsaur, M-L., Menzel, S., Lai, F-P., Espinosa, R., Concannon, P., Spielman, R. S., Hanis, C. L., Cox, N. J., Le Beau, M. M., German, M. S., Jan, L. Y., Bell, G. I. and Stoffel, M. "Isolation of a cDNA clone encoding a $K_{ATP}$ channel-like protein expressed in insulin-secreting cells, localization of the human gene to Chromosome band 21q22.1 and linkage studies with NIDDM" *Diabetes* 44: 592–596 (1995).

23. Ashford, M. J., Bond, C. T., Blair, T. A. and Adelman, J. P. "Cloning and functional expression of a rat heart $K_{ATP}$ channel" *Nature* 370: 456–459 (1994).

24. Krapivinsky, G., Gordon, E. A., Wickman, K., Velimirovic, B., Krapivinsky, L. and Clapman, D. E. "The G-protein-gated atrial K$^+$ channel $I_{KACh}$ is a heteromultimer of two inwardly rectifying K$^+$ channel proteins" *Nature* 374: 135–141 (1995).

25. Duprat, F., Lesage, F., Guillemare, E., Fink, M., Hugnot, J-P., Bigay, J., Lazdunski, M., Romey, G. and Barhanin, J. "Heterologous multimeric assembly is essential for K$^+$ channel activity of neuronal and cardiac G-protein activated inward rectifiers" *Biochem. Biophys. Res. Comm.* 212: 657–663 (1995).

26. Shuck, M. E, Bock, J. H., Benjamin, C. W., Tsai, T-D., Lee, K. S., Slightom, J. L. and Bienkowski, M. J. "Cloning and characterization of multiple forms of the human kidney ROM-K potassium channel" *J. Biol. Chem.* 269: 24261–24270 (1994).

SUMMARY OF THE INVENTION

Two unique channel polypeptides and the cDNA that codes for them, KIRK-2, and KIRK-3, have been identified and cloned. KIRK-2 is related to a rat potassium channel protein coding cDNA called BIRK-10. KIRK-2 is on chromosome 1 while KIRK-3 has no known homologs and maps to chromosome 21. DNA and Amino Acid sequences are provided. These two human K channels were compared by determining their tissue-distribution of expression, their human chromosome assignment and their electrophysiological properties when expressed in Xenopus oocytes and mammalian cells.

KIRK-2 and KIRK-3 have their cDNA sequences provided in Sequence Listings 1 and 2 and their protein sequences provided in Sequence Listings 3 and 4. cDNA molecules being about at least 80, 85, or 90 percent homologous to any of the above described DNA molecules thereof are described. Various vectors and plasmids comprising the DNA molecules of Sequence Listings 1–2 and selected derivatives thereof are described. Vectors and plasmids adapted for expression in a bacterial cell, yeast cell, or a mammalian cell are described. Use of the bacterial, yeast, or mammalian cell containing the vector or plasmid of Sequence Listings 1–2 or selected derivatives thereof, to screen for compounds that modulate human kidney ATP-gated and related potassium channel activity are described.

Also described is a method of using a mammalian, bacterial or, yeast cell as described above, to screen for compounds that modulate human kidney potassium channel activity. The method may be comprised of the following steps: a) growing cells expressing a cloned K$^+$ channel to confluence, b) equilibrating the cells of a) with a balanced salt solution, c) making baseline measurements of the equilibrated cells, d) adding one test compound or a cocktail of test compounds to the cells and recording changes in membrane potential, e) testing compounds that depolarize cells expressing the K$^+$ on wild type or mock transfected controls to establish selectivity, f) selecting the compounds that are shown to selectively block K$^+$.

DESCRIPTION OF THE PREFERRED EMBODIMENTS

Figure 1:
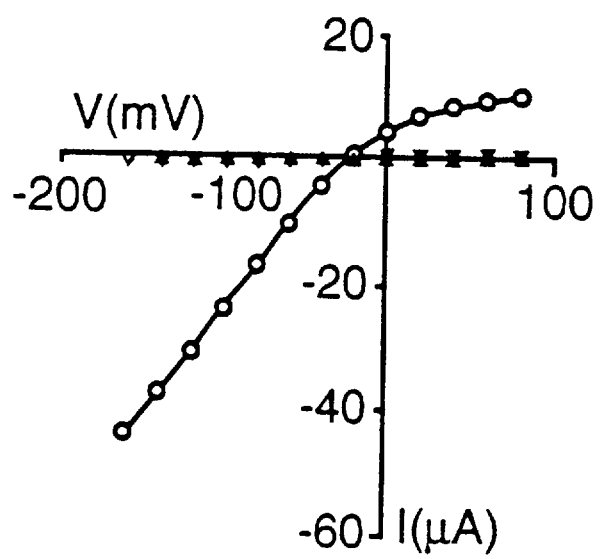

This invention relates to the cloning and isolation of human DNAs encoding potassium ATP-gated channel proteins. In one embodiment this invention comprises isolated functional cDNA clones encoding human potassium ATP-gated channel proteins, verified by using *Xenopus laevis* oocytes as an expression system for studying ion channels. Mammalian and a bacterial cell lines expressing functional human potassium ATP-gated channels at the cell surface are described, as determined by pharmacologic and physiologic methods, thus establishing the first well-defined cell lines with which to study this particular member of a family of ATP-gated channel proteins. In another embodiment the human potassium ATP-gated channels are described as a possible high volume screen for novel compounds.

Definitions.

This document uses abbreviations and terms that should be well known to those skilled in the art. Some terms are more fully described in the sections below. This document also uses the terms: KIRK 1, KIRK 2 and KIRK 3, these terms are analogous to the terms: $K_{ir}1.1$ (or "the ROM-K" or "ROMK"), $K_{ir}1.2$ and $K_{ir}1.3$, respectively.

ISOLATION AND IDENTIFICATION OF A HUMAN POTASSIUM CHANNEL DNA CLONE.

The cDNA encoding the entire open-reading frame of a BIRK 10 transcript was isolated by RT-PCR and this sequence used as a probe to determine the tissue distribution of expression of the BIRK 10 transcript in various rat organs by Northern blot analysis. Of the tissues examined, a 5.2 kb transcript was only detected in the brain and kidney. A cDNA library prepared from the latter tissue was used to isolate the human BIRK 10. A human kidney cDNA library was screened at reduced stringency with the coding sequence of rat BIRK 10. Clonal cDNAs prepared from these positives were grouped by restriction mapping and representative clones subjected to DNA sequence analysis. Comparative analysis of these cDNA sequences revealed that among the clones that exhibited high homology to rat BIRK 10, none of them appeared to contain the entire open-reading frame. In addition, a second set of related cDNAs, were also identified and the latter sequence appeared novel. Consistent with the emerging nomenclature in this field, we have named these two new human K channel cDNAs KIRK-2 and KIRK-3 (Kidney inward rectifier K channel), where the ROMK channel is referred to as KIRK-1.

DETAILS OF PROCEDURES, METHODS AND EMBODIMENTS

Cloning of rat brain BIRK 10.

An on-line BLAST search of the GenBank database available through the National Center for Biotechnology Information (NCBI) using the human ROMK1 cDNA as the query sequence (GenBank accession #U12541) identified a related rat cDNA sequence (GenBank accession #X83858). This cDNA had been cloned from rat brain (4) RNA and was referred to as brain inward rectifier K channel 10 (BIRK 10). Based on the cDNA sequence in GenBank, a sense oligonucleotide primer (C12-A 5' CGC-TTT-GAA-TTC-ATG-ACA-TCA-GTT-GCC-AAG-GTC-TAT-TA 3' SEQ. ID. NO. 5 alignment positions 1–26 in X83858) and an antisense oligonucleotide primer (C12-B 5' CGC-TTT-GAA-TTC-TCA-GAC-GTT-ACT-AAT-GCG-CAC-ACT-A SEQ. ID. NO. 6, alignment positions 1116–1140 in X83858) were synthesized. Total RNA (10 µg) isolated from rat brain was reversed transcribed using and oligo dT primer and reverse transcriptase. A portion of the resulting cDNA was then amplified in the PCR employing the C12-A and C12-B primers. The 1.2 kb product was digested to completion with EcoRI and subcloned into the EcoRI site of the plasmid vector pBK-CMV to yield pBK-CMV/BIRK 10.

Cloning of human kidney BIRK 10.

Preliminary Northern blot analysis using the rat BIRK 10 cDNA as a probe revealed that in addition to the brain, BIRK 10 was also expressed in kidney. A human kidney cDNA library in the bacteriophage $\lambda^{gt10}$ was plated on *E. coli* strain DP50supF (500,000 recombinants). The rat BIRK 10 cDNA was excised from the plasmid pBK-CMV/BIRK 10 by digestion with EcoRI followed by preparative gel analysis. A portion of this fragment was then random prime labeled to a specific activity of >1.0×10$^9$ dpm $^{32}$P/$\mu$g DNA using $\alpha$-$^{32}$P-dATP and Klenow DNA polymerase. Replicate lifts of the bacteriophage library were screened with the $^{32}$P-labeled rat BIRK 10 EcoRI fragment (5×10$^6$ dpm/ml) overnight at 65° C. The filters were then washed with 0.3M NaCl/0.1% SDS at 65° C. and the coordinates of radioactivity on the filters determined by autoradiography at −70° C. with intensifying screens. Replicate positive bacteriophage clones from the primary screen were isolated from the agar plates and cloned by limiting dilution followed by rescreening as described above. Fourteen distinct clonal bacteriophage stocks prepared from the hybridization positive clones were used to prepare $\lambda$-DNA by infection of *E. coli* strain DP50supF at a multiplicity of infection of 0.02. Bacteriophage DNA was prepared for the infected cultures using polyethylene glycol precipitation of the bacteriophage particles followed by destruction of the bacteriophage protein coat. Bacteriophage DNAs prepared in this manner were digested with EcoRI to produce the cDNA inserts. The size of the liberated fragments was determined by agarose gel electrophoresis. Based on the restriction mapping, 4 representative clones were selected for DNA sequence analysis. DNA sequencing of the cDNA inserts was performed by cycle sequencing dideoxy-chain termination method (AmpliTaq kit, Perkin-Elmer-Cetus, Norwalk, Connecticut). In the case of KIRK-2, a genomic clone was also isolated from a human genomic library in the vector $\lambda^{FIXII}$ using one of the partial cDNA clones obtained from the human kidney cDNA library as described above.

Northern blot analysis and human chromosome assignment.

The tissue distribution of expression of both KIRK-2 and KIRK-3 was determined by Northern blot analysis using MTN blots purchased from Clonetech (Palo Alto, Calif.). For KIRK-2, a 1.3 kb EcoRI fragment containing the 3' end of the KIRK-2 open-reading frame and approximately 0.6 kb of 3' untranslated sequence was used as a probe. For KIRK-3, a 1.4 kb EcoRI/MunI fragment containing the entire open reading frame of KIRK-3 was used as a probe. In either case, the fragments were random prime labeled using $\alpha$-$^{32}$P-dATP as described above followed by hybridization to Nylon membranes containing poly A$^+$ RNAs from various human tissues or human brain regions as previously described (26). Somatic cell hybrid panel blots were purchased from Oncor (Gaithersburg, Md.) and hybridized to either of the KIRK cDNA probes described above under the conditions recommended by the manufacture (50% formamide/6X SSC/10% Dextran Sulfate/1.0% SDS/50 $\mu$g/ml calf thymus DNA at 50° C. overnight). In all cases, the blots were washed at high stringency (0.1X SSC) and labeled bands visualized by autoradiography.

Heterologous expression of KIRK-2 and KIRK-3.

The open-reading frame of KIRK-2 was engineered for expression in Xenopus oocytes using the PCR. Sense (5' CAG-AAG-TTA-AGT-CGA-CAT-GAC-GTC-AGT-TGC-CAA-GGT-GTA-TT 3' SEQ. ID. NO. 7) and antisense (5' CAG-AAG-TTA-AGC-GGC-CGC-(T)$_{28}$-CAG-ACA-TTG-CTG-ATG-CGC-ACA-CT 3' SEQ. ID. NO. 8) primers that flank the open-reading frame of KIRK-2 were used to PCR amplify this region of the genomic clone for KIRK-2 (20 cycles with 0.5 $\mu$g template/reaction). See Shuck, M. E, Bock, J. H., Benjamin, C. W., Tsai, T-D., Lee, K. S., Slightom, J. L. and Bienkowski, M. J. "Cloning and characterization of multiple forms of the human kidney ROM-K potassium channel." *J. Biol. Chem.* 269: 24261–24270 (1994), incorporated by reference.

The product was digested to completion with SalI and NotI and cloned into the plasmid vector pSPORT-1 to yield pSPORT/KIRK-2. For KIRK-3, the original $\lambda$-clone was double digested with EcoRI and MunI and subcloned into the plasmid vector pBK-CMV to yield pBK-CMV/KIRK-3. This plasmid was then double-digested with EcoRI/AccI and directionally cloned into pSPORT/rROMK1 to introduce the poly A tail from the rat ROMK1 cDNA (1). See, Ho, K., Nichols, C. G., Lederer, W. J., Lytton, J., Vassilev, P. M., Kanazirska, M. V. and Hebert, S. C. "Cloning and expression of an inwardly rectifying ATP-regulated potassium channel." *Nature* 362: 31–38 (1993), incorporated by reference. In each case, cRNA was synthesized from NotI-linearized template use T7 RNA polymerase as previously described (26), incorporated by reference.

Oocytes were collected under tricaine (3-aminobenzoic acid ethyl ester, 0.17%; Sigma, St. Louis, Mo.) and cold-induced anesthesia from adult African clawed frogs, *Xenopus laevis* (Nasco, Ft. Atkinson, Wis.), and defolliculated by blunt dissection in Ca$^{2+}$ free ND-96 following 40 minutes incubation in 2 mg/ml collagenase (Type II; Sigma, St. Louis, Mo.). ND-96 consisted of 96 mM NaCl, 2 mM KCl, 1 mM MgCl$_2$, 0.3 mM CaCl$_2$, 5 mM HEPES, pH 7.6.The following day, a glass injection pipette manually broken to ~15 $\mu$m tip diameter was used to inject oocytes with 46 nl of polyadenylated cRNA dissolved in water at 15, 30 or 100 ng/$\mu$l resulting in injection of 0.6, 1.2, or 4 ng of cRNA. Prior to recordings, oocytes were maintained 2–7 days at 20° C. in ND-96 supplemented with gentamycin (50 mg/ml; Bio-Whittaker, Walkersville, Md.) and sodium-pyruvate (2.5 mM; Sigma).

Electrophysiological recordings were conducted at room temperature. Oocyte resting membrane potential was measured in ND-96 using 30–80 M$\Omega$ glass microelectrodes filled with 3M KCl For two-microelectrode voltage-clamp recordings, the voltage-measuring pipette had resistances of 1.5 to 2.0 M$\Omega$, while the current-injection pipette had resistances of 0.7–0.9 M$\Omega$; both pipettes were filled with 3M KCl. All voltage-clamp recordings were conducted in bath solutions containing 1 mM MgCl$_2$, 0.3 mM CaCl$_2$, and 5 mM HEPES. For experiments conducted in 50 mM K$^+$, the solution contained 50 mM KCl and 50 mM NaCl. For lower potassium concentrations, this solution was mixed with an identical solution in which choline was substituted for potassium. Pairs of solutions at pH 5.4 and 8.4, containing 50 mM KCl and either 50 mM potassium-acetate or 50 mM potassium-hydrogen phthalate (biphthalate; Sigma, St. Louis, Mo.) were mixed to vary pH.

Two-microelectrode, voltage-clamp recordings were conducted using the GeneClamp 500 (Axon Instruments, La Jolla, Calif.) interfaced with a 486 Computer running the PCLAMP 6.0 (Axon Instruments, La Jolla, Calif.) suite of programs. Currents were filtered at 2 kHz and sampled every 100 $\mu$s. Current amplitude was measured during the last 4 ms of a 400 ms test pulse. Data were analyzed and plotted using PCLAMP 6.0 and SIGMA PLOT 5.0 (Jandel Scientific, San Rafael, Calif.). Statistical significance was determined by the Student's T-test.

Composition of the cDNA's.

The DNA sequence and predicted amino acid sequence of hKIRK-2 and hKIRK-3 are shown in Sequence Listings 1–4. The human KIRK-2 (BIRK 10) sequence, derived from a composite of both cDNA and genomic sequence, contains a 1128 bp open-reading frame that encodes a 376 amino acid polypeptide that showed 91% shared identity with the rat BIRK 10 amino acid sequence. Consistent with the predicted structures of other members of this family of K channels, the sequence of human KIRK-2 contains two putative transmembrane domains that flank an H-5 region that forms an integral part of the $K^+$-selective pore. More detailed analysis of the predicted amino acid sequence of hKIRK-2 using the MOTIF algorithm revealed 2 canonical Asn-linked glycosylation acceptor sites, 6 consensus acceptor sites for casein kinase II, and 6 consensus PKC acceptor sites. Also, the predicted Walker Type A ATP binding motif ($GX_4GKX_7(I/V)$), is conserved in the hKIRK-2 sequence.

The hKIRK-3 cDNAs predicted an 1125 bp open-reading frame that encodes a 375 amino acid polypeptide that was 62% identical and 47% identical to the hKIRK-2 and hKIRK-1 amino acid sequences, respectively. The two putative transmembrane domains flanking an H-5 region were also evident in the predicted amino acid sequence of hKIRK-3. Analysis of the predicted amino acid sequence of hKIRK-3 using the MOTIF algorithm revealed 2 canonical acceptor sites for Asnglycosylation, 5 consensus sites for casein kinase II, 4 consensus PKC. sites and 3 consensus tyrosine kinase acceptor sites near the C-terminus of the protein. In contrast to the hKIRK-1 and hKIRK-2 sequences, the consensus Walker Type A ATP-binding motif $GX_4GKX_7$ (I/V), is not conserved in the hKIRK-3 sequence.

Heterologous expression of KIRK 2 and KIRK 3 in Xenopus oocytes.

The K channels synthesized following injection of either KIRK 2 or KIRK 3 polyadenylated cRNAs into Xenopus oocytes were studied using standard electrophysiological procedures. Forty-eight hours post injection of 4 ng of KIRK 2 cRNA, the oocyte resting membrane potential was hyperpolarized by 49 mV (−93±3 mV (n=25)) when compared to water-injected oocytes (−44±3 mV, n=16, P<0.001)). The observed resting membrane potential of KIRK 2-injected oocytes was close to the calculated potassium equilibrium potential of −106 mV at 2 mM extracellular $K^+$ and assuming 130 mM intracellular $K^+$. Thus, the KIRK 2-injected cells expressed a potassium-selective ion channel that was not detected in water-injected cells. In contrast, injection of oocytes with up to 4 ng of polyadenylated KIRK 3 cRNA did not apparently significantly alter the membrane potential compared to water injected oocytes (−49±4 mV (n=17)- versus- −44±3 mV (n=17), respectively). The reasons for this apparent anomaly remain unknown at this time.

FIG. 1 shows current voltage curves from a single batch of oocytes injected with either water =▽; KIRK 2=$K_{ir}$1.2=○; or KIRK 3, =$K_{ir}$1.3=▲. The X-axis shows voltage (mV) the Y-axis is current ($\mu$A). Oocytes expressing KIRK 2 channels displayed large inward currents in response to voltage steps negative of the potassium equilibrium potential (−20 mV in 50 mM $K^+$) and these currents were not detected in water-injected cells. For example, whole-cell current measured during a test pulse to −140 mV from a holding potential of −20 mV in 50 mM $K^+$ was −4.4±0.5 (n=4) and −22.4±4.9 $\mu$A (n=7) in oocytes injected with 1.2 or 4 ng of KIRK 2 cRNA, respectively, but was only −125±13 nA in water-injected cells (n=8). Consistent with the lack of membrane hyperpolarization in oocytes injected with KIRK 3 cRNA, the whole-cell current was actually smaller than the current measured in water-injected oocytes (−161±27 nA at −140 mV, n=4). KIRK 2 currents measured during voltage steps positive of the potassium equilibrium potential were distinctly smaller than those measured during steps negative of the $K^+$ equilibrium potential, creating a mild, inward rectification.

Figure 2A:
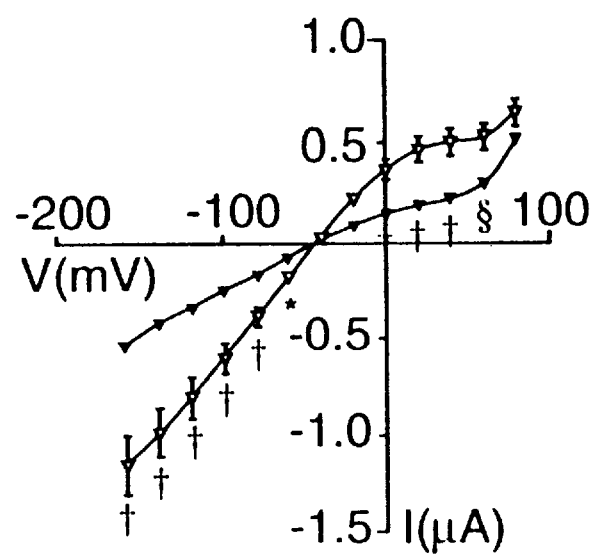
Figure 2B:
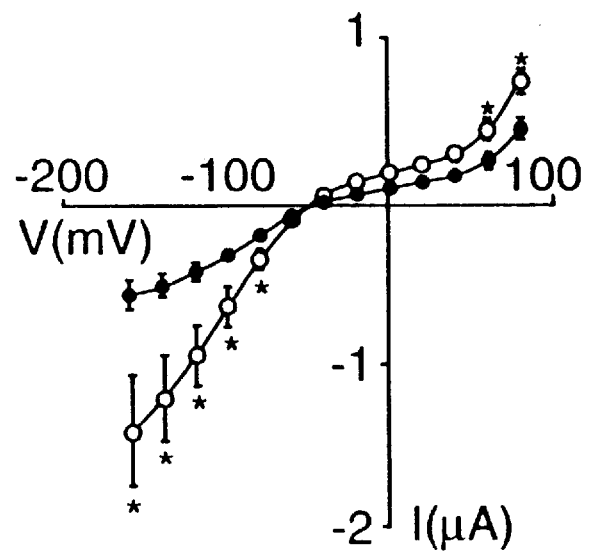

Some KIRK channel pore-forming polypeptides fail to produce detectable currents when expressed alone in oocytes. Co-expression of KIRK channel subunits has produced both reconstitution of channel activity, Krapivinsky, G., Gordon, E. A., Wickman, K., Velimirovic, B., Krapivinsky, L. and Clapman, D. E. "The G-protein-gated atrial $K^+$ channel $I_{KACh}$ is a heteromultimer of two inwardly rectifying $K^+$ channel proteins." *Nature* 374: 135–141 (1995) and Duprat, F., Lesage, F., Guillemare, E., Fink, M., Hugnot, J-P., Bigay, J., Lazdunski, M., Romey, G. and Barhanin, J. "Heterologous multimeric assembly is essential for $K^+$ channel activity of neuronal and cardiac G-protein activated inward rectifiers." *Biochem. Biophys. Res. Comm.* 212: 657–663 (1995), as well as decreases in currents compared to those produced by homomeric co-expression. Tucker, S. J., Bond, C. T., Herson, P., Pessia, M., and Adelman, J. P. (1996) "Inhibitory interactions between two inward rectifier $K^+$ channel subunits mediated by the transmembrane domains." *J. Biol. Chem.* 271: 5866–5870. The effect of coexpression of KIRK 3 cRNA with suboptimal amounts of either KIRK 1 (FIG. 2A) or KIRK 2 (FIG. 2B) cRNA (0.6 ng) was determined and the results are shown in FIGS. 2A and 2B. In FIGS. 2A and 2B the axis' are the same as for FIG. 1. In FIG. 2A, KIRK 1=$K_{ir}$1.1=▽ and KIRK 1 plus KIRK 3=$K_{ir}$ 1.1 plus $K_{ir}$ 1.3=▼. In FIG. 2B, KIRK 2=$K_{ir}$ 1.2=○ and KIRK 2 plus KIRK 3=$K_{ir}$ 1.2 plus $K_{ir}$1.3=●. Expression of KIRK 1 or KIRK 2, channels alone produced −1.14±0.15 (n=5) and −1.14±0.34 (n=5) $\mu$A of current, respectively, at a holding potential of −160 mV. Co-injection of a 6.7-fold excess of KIRK 3 decreased KIRK 1 and KIRK 2 currents by 54% and 51% to −0.52±0.03 (p<0.005, n=5) $\mu$A and −0.56±0.09 (p<0.05, n=4) $\mu$A, respectively.

The KIRK 2 channel forms a $K^+$-selective $Ba^{2+}$-sensitive channel.

The dependence of reversal potential on extracellular $K^+$ and $Ba^{2+}$ was determined, see FIGS. 3. The dependence of reversal potential on extracellular $K^+$ is similar to that expected for a potassium-selective channel at room temperature (slope-per-decade change of 55 mV. The effect of varying extracellular $[K_+]$ on the current-voltage relationship of KIRK 2 expressing oocytes was investigated and the membrane conductance of KIRK 2 was dependent on extracellular $[K^+]$, FIG. 3A. The axis for FIG. 3A is the same as for FIG. 1. In FIG. 3A, 5 mM $K^+$=○, 10 mM $K^+$=●, 25 mM $K^+$=▽, 50 mM $K^+$=▼.

Figure 3A:
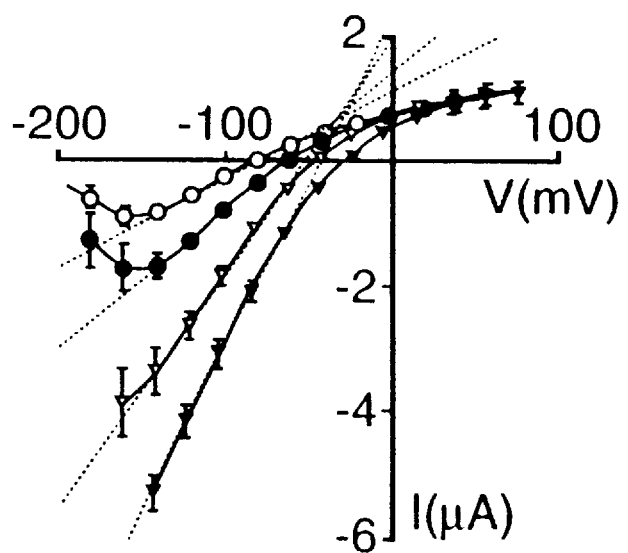
Figure 3B:
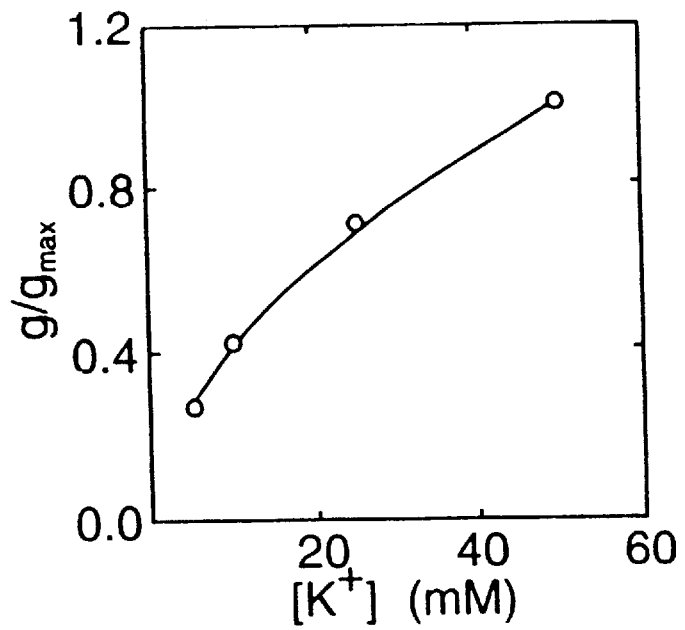

The relationship $g=C[K^+]_0^Z$ relates conductance, g, obtained by fitting the linear portion of the current-voltage curves (dotted lines), to external potassium concentration. C and Z were varied to produce the best fit of these data, FIG. 3B. In FIG. 3B the y-axis is g/gmax and the x-axis is $[K^+]$(mM). The Z value for KIRK 2 was 0.54, similar to the values of 0.62, 0.47, and 0.38–0.49 for the cardiac IK1 (28,29), mouse macrophage IRK1 (3), and human ROMK isoforms 1–3, respectively. The square root dependence of membrane conductance on extracellular $K^+$ concentration is typical of the multi-ion pore of inward rectifier $K^+$ channels.

Figure 3C:
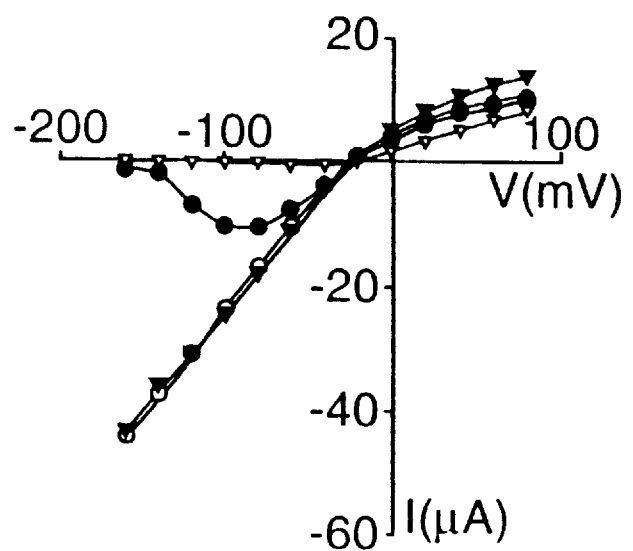

Application of $Ba^{2+}$ (0.03 $\mu$M to 10 mM) produced a reversible, concentrationdependent inhibition of KIRK 2 current, FIG. 3C, n=8). In FIG. 3C, the axis are the same as in FIGS. 1 and 2, control =○, 30 $\mu$M $Ba^{2+}$=●, 300 $\mu$M Ba$^{2+}$=▽, and wash =▽. The inhibition by Ba$^{2+}$ was time- and voltage-dependent as expected for the open-channel block typical of the effects of Ba$^{2+}$ on native and cloned inward-rectifier K$^+$ channels.

Figure 3D:
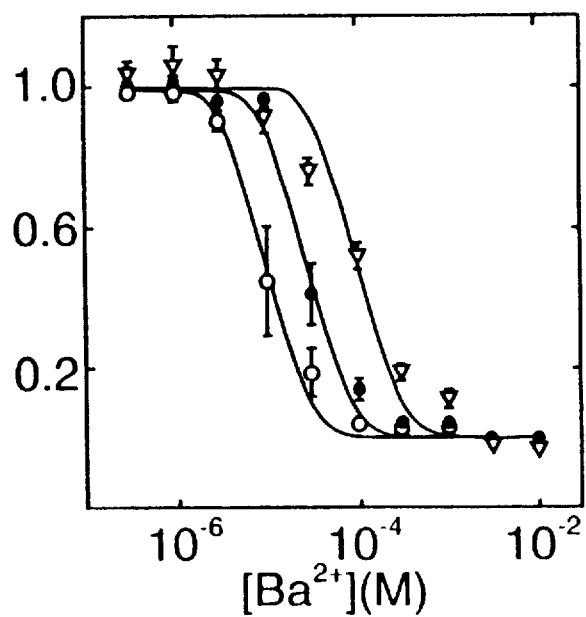
Figure 3E:
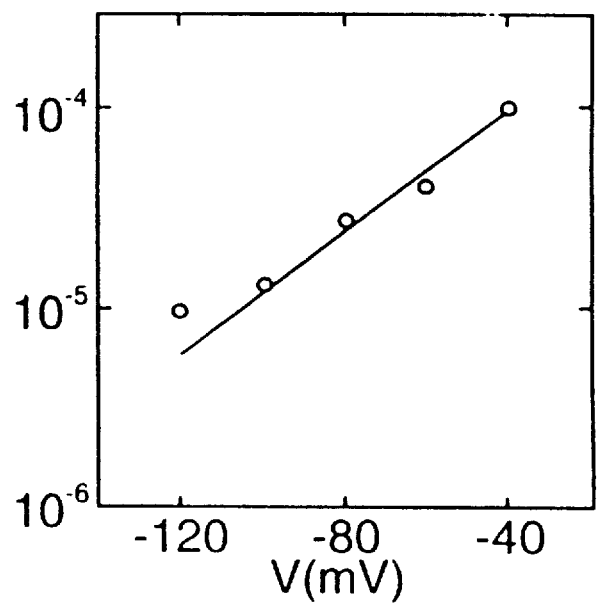

The concentration-dependence of KIRK 2 inhibition by Ba$^{2+}$ at three different holding potentials is shown in FIG. 3D. In FIG. 3D, n=8) the x-axis is the Relative Current and the y-axis the concentration of Ba$^{2+}$(M); the three curved lines show −120 mV=○, −80 mV=●, and −40 mV =▽. These data were fitted by a simple logistic equation with a Hill coefficient of 2 and the resulting $K_i$ values were plotted versus membrane potential in FIG. 3E. Fit of these data by the Woodhull equation suggests that the Ba$^{2+}$ binding site senses 46% of the transmembrane electric field, in reasonable agreement with previously published results in BIRK-10 injected oocytes. Inhibition of KIRK 2 by Cs$^+$ was also reversible and voltage-dependent, being apparent only at the most negative potentials tested, but was far less effective than block by Ba$^{2+}$ (n=6, data not shown). Thus KIRK 2 encodes an inwardly-rectifying, Ba$^{2+}$- and Cs$^+$-sensitive potassium channel.

Tissue Distribution of Expression and Human Chromosome Assignment.

KIRK-2 is expressed at high levels in whole brain and kidney and few other tissues. KIRK-3 also showed a limited tissue distribution of expression (kidney>pancreas>>lung) and multiple transcript sizes were detected. In contrast to KIRK-2 which was most abundant in the brain, no KIRK-3 transcripts were detected in brain.

The human Chromosome location of the KIRK-2 and KIRK-3 was determined by Southern blot analysis of genomic DNA prepared from a panel of mouse/human or hamster/human somatic cell hybrids. The KIRK-2 and KIRK-3 genes localized to human Chromosome 1 and human Chromosome 21, respectively.

PREPARATION OF A BIOASSAY USING THE EXPRESSION SYSTEMS BASED ON THE PROTEINS DESCRIBED HEREIN

By making appropriate modifications to the procedures described in: Bienkowski and Groppi, WO 94/19464, PCT/US94/01210, published 1 Sep. 1994, "Human DNA sequence encoding a kidney ATP-dependent potassium channel," incorporated by reference, and using those procedures plus other appropriate procedures and techniques disclosed in other references cited herein, plus references and knowledge generally known to one skilled in the art, in combination with the information and sequences described herein, one skilled in the art should be able to prepare suitable vectors and/or plasmids comprising a DNA molecule that is of the KIRK-2 or KIRK-3 type, Sequence Listings 1 and 2, or derivatives thereof having at least about 80, 85, or preferably 90 percent homology to KIRK-2 or KIRK-3, that are adapted for expression in a bacterial cell, a mammalian cell or a yeast cell and by using these bacterial, mammalian or yeast cells having those expressing vectors or plasmids one skilled in the art would be able to develop a method of using those cells to screen for compounds that modulate human kidney potassium channel activity.

What is claimed is:

1. An isolated nucleic acid that codes for the protein of SEQ. ID. NO. 4.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2896 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
CTGATCTGAT    CTTATCTTCT    CTCTTCTTTT    CTTTGAGTGT    GAATTTTCCT    GTTTCCCCCA        60

GGCTGGAGTG    CAGTGGCGCG    ATGTCGGCTC    ACTGCAACCT    CTGTCTCCCG    GGTTCAAGCG       120

ATTCTCCTGC    CTCAGCCTCC    TGAGTAGCTG    GGACTACAGG    CGCATGCCAC    CATGCCAGC        180

TAATTTTTGT    ATTTTAGTA     GAGACAGGGT    TTTGCCTTGT    TGGCCAGGCT    GGTCTTGAAC       240

TCCTGACCTC    AGGCGATCCA    CCCGCCTCGG    CCCCTGCACA    GTGCCTGGCA    CATAGCAAGT       300

GCTCAATAAA    TATTTGGTAA    GACAAGAACA    CATAAGCGAC    ATTCAAATGA    ATGTCAATTC       360

CTCCCTCCCA    TGGGGTGAGG    GTTAGGAGTC    AGCTGGATTT    CTACGATAAC    CTCCATTATG       420
```

-continued

| | | | | | |
|---|---|---|---|---|---|
| CTGTCTTGCT | CCCTCCAGAT | GACGTCAGTT | GCCAAGGTGT | ATTACAGTCA | GACCACTCAG | 480 |
| ACAGAAAGCC | GGCCCCTAAT | GGGCCCAGGG | ATACGACGGC | GGAGAGTCCT | GACAAAAGAT | 540 |
| GGTCGCAGCA | ACGTGAGAAT | GGAGCACATT | GCCGACAAGC | GCTTCCTCTA | CCTCAAGGAC | 600 |
| CTGTGGACAA | CCTTCATTGA | CATGCAGTGG | CGCTACAAGC | TTCTGCTCTT | CTCTGCGACC | 660 |
| TTTGCAGGCA | CATGGTTCCT | CTTTGGCGTG | GTGTGGTATC | TGGTAGCTGT | GGCACATGGG | 720 |
| GACCTGCTGG | AGCTGGACCC | CCCGGCCAAC | CACACCCCCT | GTGTGGTACA | GGTGCACACA | 780 |
| CTCACTGGAG | CCTTCCTCTT | CTCCCTTGAA | TCCCAAACCA | CCATTGGCTA | TGGCTTCCGC | 840 |
| TACATCAGTG | AGGAATGTCC | ACTGGCCATT | GTGCTTCTTA | TTGCCCAGCT | GGTGCTCACC | 900 |
| ACCATCCTGG | AAATCTTCAT | CACAGGTACC | TTCCTGGCGA | AGATTGCCCG | GCCCAAGAAG | 960 |
| CGGGCTGAGA | CCATTCGTTT | CAGCCAGCAT | GCAGTTGTGG | CCTCCCACAA | TGGCAAGCCC | 1020 |
| TGCCTCATGA | TCCGAGTTGC | CAATATGCGC | AAAAGCCTCC | TCATTGGCTG | CCAGGTGACA | 1080 |
| GGAAAACTGC | TTCAGACCCA | CCAAACCAAG | GAAGGGGAGA | ACATCCGGCT | CAACCAGGTC | 1140 |
| AATGTGACTT | CCAAGTAGA | CACAGCCTCT | GACAGCCCT | TCCTTATTCT | ACCCCTTACC | 1200 |
| TTCTATCATG | TGGTAGATGA | GACCAGTCCC | TTGAAAGATC | TCCCTCTTCG | CAGTGGTGAG | 1260 |
| GGTGACTTTG | AGCTGGTGCT | GATCCTAAGT | GGGACAGTGG | AGTCCACCAG | TGCCACCTGT | 1320 |
| CAGGTGCGCA | CTTCCTACCT | GCCAGAGGAG | ATCCTTTGGG | CTACGAGTT | CACACCTGCC | 1380 |
| ATCTCACTGT | CAGCCAGTGG | TAAATACATA | GCTGACTTTA | GCCTTTTGA | CCAAGTTGTG | 1440 |
| AAAGTGGCCT | CTCCTAGTGG | CCTCCGTGAC | AGCACTGTAC | GCTACGGAGA | CCCTGAAAAG | 1500 |
| CTCAAGTTGG | AGGAGTCATT | AAGGGAGCAA | GCTGAGAAGG | AGGGCAGTGC | CTTAGTGTG | 1560 |
| CGCATCAGCA | ATGTCTGATG | ACCTGTTCCC | ACTCCCCAT | TCCTCTGGTC | TCTTTTCCTC | 1620 |
| TCTTCCAATG | CCCTGGTAAG | GAATACTACC | CGGGTTTACT | GGAGATCCCC | CGAAGCACCC | 1680 |
| ATCCTCCACT | CCCTCTTCTT | TAACCCAGTG | GCCTGTTGGT | AGCTTAGGCC | AACTGGAGTC | 1740 |
| CAGGTTCGCC | TCCCACTGTC | CCCTTTCCAC | TTCCCCAGCT | TCTGCCCCAA | TACACATACC | 1800 |
| TCCCTTAAGC | CAGGATGGGG | GAAAGAGTGG | GATTAGGCTG | AAGTGGCTTA | GAAGGCCTCA | 1860 |
| GCCATGCTTG | GATACTCACA | TTAGGAGGAC | CATGTGGTTG | GAAGGATAGA | CTGCCCCCTA | 1920 |
| CCTCCCACCA | CCACCATGAA | GTTTGGTGAC | TTGAGGCTGG | AGCTCCCTCT | GTTACCTTTC | 1980 |
| CATCTAGCAA | GTTCCCAAAG | GCAAGACTCT | CTCTGATGGT | CACTTTGTGG | TCTGTGCTTT | 2040 |
| CAGAAATACA | GGAATCTGAT | ATCAACATAT | CCTAGGGTTT | CTACCAATCT | CTGTTGAAAG | 2100 |
| AAGCCAGGGT | TTGCCACTGT | GAAGCTTGAT | TTCTGCTGGT | GACTTCTGAC | CATAAGCTAG | 2160 |
| AACCATGGTC | GCCACTGTTT | TCCCTCTGTA | GTTTCTCAAG | TGAACACTCT | CAGGATACCC | 2220 |
| AGTTCCCTCA | TAGCCTCTGT | TCTCAGAGAA | TTGGAGTTGG | CCCAAGAAAC | ATAAACATAT | 2280 |
| AACCACCCAT | ATCTATCCTG | GATTCTGAAC | TCTTCAATTT | GGAGTGACTA | ACACAAGTTG | 2340 |
| TTATCTAAAC | CTTTAAACCT | ATCTTCCAGG | CAGCCCAGAG | AAGATCTGTT | TCCCTGTGTC | 2400 |
| CTGTGAATGG | AAGGACCCAA | GCCAATATGT | TCCTTTGAAA | AGAGTCCAGT | ACCCAGGCCC | 2460 |
| CATGGAAAGG | TCTGAAAATA | ATATTCCAGA | TTACACTGTA | CCTGGCTTCT | CTTCTTCCTT | 2520 |
| TCCTGCTCAG | CCTAGATCCT | TCTTCCTTAA | CCCCAACTCT | TGGGAGAAG | GGAGGGAAAA | 2580 |
| TGCAAGGGCC | TTCCTCTCTT | AACACGGATG | CTCAAGTAAA | ACTAGATTCA | CAGGGCACAG | 2640 |
| ATTCCCCAGA | AAGTTAACAC | AATCCCACCA | TGAGGGATGG | GTAAATTCTC | AGATTTCCAA | 2700 |
| ACTGCTGTAC | AGAGCCTCTG | AGAATTGGTG | ATGCTTTGTT | AAGGTTTGGG | CAGGAGCAGA | 2760 |
| ACTCTGTGGC | TGGCAGCCAC | TATTCTCAGT | TACACCTCCC | AGTGCCCTTC | TGAAAAGTGC | 2820 |

| CAGCTATTTC | ATTAGGCAAT | GCTGGAAGGA | AATGAAATTA | TACCTTCTGA | TCAAATAACC | 2880 |
| ATGGCTTCCC | TCAGCC | | | | | 2896 |

(2) INFORMATION FOR SEQ ID NO:2:

(i) SEQUENCE CHARACTERISTICS:
        (A) LENGTH: 1625 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: N-terminal (xi) SEQUENCE DESCRIPTION: SEQ ID NO:2:

| GAATTCCGGG | TTCTACCTGC | CTTGAAGAAG | ACACCTGACC | TGCGGAGTGA | GTGACCAGTG | 60 |
| TTTCCAGAGC | CTGGCAATGG | ATGCCATTCA | CATCGGCATG | TCCAGCACCC | CCTGGTGAA | 120 |
| GCACACTGCT | GGGGCTGGGC | TCAAGGCCAA | CAGACCCCGC | GTCATGTCCA | AGAGTGGGCA | 180 |
| CAGCAACGTG | AGAATTGACA | AAGTGGATGG | CATATACCTA | CTCTACCTGC | AAGACCTGTG | 240 |
| GACCACAGTT | ATCGACATGA | AGTGGAGATA | CAAACTCACC | CTGTTCGCTG | CCACTTTTGT | 300 |
| GATGACCTGG | TTCCTTTTTG | GAGTCATCTA | CTATGCCATC | GCGTTTATTC | ATGGGGACTT | 360 |
| AGAACCCGAT | GAGCCCATTT | CAAATCATAC | CCCCTGCATC | ATGAAAGTGG | ACTCTCTCAC | 420 |
| TGGGGCGTTT | CTCTTTTCCC | TGGAATCCCA | GACAACCATT | GGCTATGGAG | TCCGTTCCAT | 480 |
| CACAGAGGAA | TGTCCTCATG | CCATCTTCCT | GTTGGTTGCT | CAGTTGGTCA | TCACGACCTT | 540 |
| GATTGAGATC | TTCATCACCG | GAACCTTCCT | GGCCAAAATC | GCCAGACCCA | AAAAGCGGGC | 600 |
| TGAGACCATC | AAGTTCAGCC | ACTGTGCAGT | CATCACCAAG | CAGAATGGGA | AGCTGTGCTT | 660 |
| GGTGATTCAG | GTAGCCAATA | TGAGGAAGAG | CCTCTTGATT | CAGTGCCAGC | TCTCTGGCAA | 720 |
| GCTCCTGCAG | ACCCACGTCA | CCAAGGAGGG | GGAGCGGATT | CTCCTCAACC | AAGCCACTGT | 780 |
| CAAATTCCAC | GTGGACTCCT | CCTCTGAGAG | CCCCTTCCTC | ATTCTGCCCA | TGACATTCTA | 840 |
| CCATGTGCTG | GATGAGACGA | GCCCCCTGAG | AGACCTCACA | CCCCAAAACC | TAAAGGAGAA | 900 |
| GGAGTTTGAG | CTTGTGGTCC | TCCTCAATGC | CACTGTGGAA | TCCACCAGCG | CTGTCTGCCA | 960 |
| GAGCCGAACA | TCTTATATCC | CAGAGGAAAT | CTACTGGGGT | TTTGAGTTTG | TGCCTGTGGT | 1020 |
| ATCTCTCTCC | AAAAATGGAA | AATATGTGGC | TGATTTCAGT | CAGTTTGAAC | AGATTCGGAA | 1080 |
| AAGCCCAGAT | TGCACATTTT | ACTGTGCAGA | TTCTGAGAAA | CAGCAACTCG | AGGAGAAGTA | 1140 |
| CAGGCAGGAG | GATCAGAGGG | AAAGAGAACT | GAGGACACTT | TTATTACAAC | AGAGCAATGT | 1200 |
| CTGATCACAG | GGGCGCCATC | CAGGTTTAAC | CCTGCAAGCT | GTTTCCACAT | CAGAACTCCC | 1260 |
| TTCAAACACA | AAGATTGCTG | TGAAAACGAA | AATGTGTAGA | CGCACTCTCA | AAAACTGCAC | 1320 |
| GGACATACAA | AATCAATCTT | TTCCTTTGAT | CTTGTGGCTA | AACCAGCATT | TCTGTGTTTG | 1380 |
| AGAGATTTCC | TGTTAGGTGC | TTCGTCTGAA | AGTGAACTCT | CATAATTCAA | ATTGTATAAA | 1440 |
| ATAAAGCTAC | ATTTCTAAGA | GCTTGGTGTA | GGGCAATTGG | AATAATGTCC | TGTTAGATAA | 1500 |
| ACAGACATTT | AGCAATGCTG | ACATTAAAAG | GAAATGTATT | TCTATACAAG | ATTATTAGCT | 1560 |
| GTAATACAAG | ATATTTATTT | AACCAATGAC | CTTATGGCTG | AGAGTTGAAT | TGTGGTTCAG | 1620 |
| TATTC | | | | | | 1625 |

( 2 ) INFORMATION FOR SEQ ID NO:3:

( i ) SEQUENCE CHARACTERISTICS:
        ( A ) LENGTH: 380 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
Met Thr Ser Val Ala Lys Val Tyr Tyr Ser Gln Thr Thr Gln Thr Glu
 1               5                  10                  15

Ser Arg Pro Leu Met Gly Pro Gly Ile Arg Arg Arg Arg Val Leu Thr
                20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
        50                  55                  60

Arg Tyr Lys Leu Leu Leu Phe Ser Ala Thr Phe Ala Gly Thr Trp Phe
 65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
               100                 105                 110

His Thr Leu Thr Gly Ala Phe Leu Phe Ser Leu Glu Ser Gln Thr Thr
            115                 120                 125

Ile Gly Tyr Gly Phe Arg Tyr Ile Ser Glu Glu Cys Pro Leu Ala Ile
        130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335
```

```
Ala  Ser  Pro  Ser  Gly  Leu  Arg  Asp  Ser  Thr  Val  Arg  Tyr  Gly  Asp  Pro
               340                      345                          350

Glu  Lys  Leu  Lys  Leu  Glu  Glu  Ser  Leu  Arg  Glu  Gln  Ala  Glu  Lys  Glu
          355                      360                      365

Gly  Ser  Ala  Leu  Ser  Val  Arg  Ile  Ser  Asn  Val  Xaa
          370                 375                      380
```

( 2 ) INFORMATION FOR SEQ ID NO:4:

( i ) SEQUENCE CHARACTERISTICS:
        ( A ) LENGTH: 376 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Met  Asp  Ala  Ile  His  Ile  Gly  Met  Ser  Ser  Thr  Pro  Leu  Val  Lys  His
1                        5                       10                          15

Thr  Ala  Gly  Ala  Gly  Leu  Lys  Ala  Asn  Arg  Pro  Arg  Val  Met  Ser  Lys
               20                      25                      30

Ser  Gly  His  Ser  Asn  Val  Arg  Ile  Asp  Lys  Val  Asp  Gly  Ile  Tyr  Leu
          35                      40                      45

Leu  Tyr  Leu  Gln  Asp  Leu  Trp  Thr  Thr  Val  Ile  Asp  Met  Lys  Trp  Arg
     50                      55                      60

Tyr  Lys  Leu  Thr  Leu  Phe  Ala  Ala  Thr  Phe  Val  Met  Thr  Trp  Phe  Leu
65                      70                      75                          80

Phe  Gly  Val  Ile  Tyr  Tyr  Ala  Ile  Ala  Phe  Ile  His  Gly  Asp  Leu  Glu
               85                      90                      95

Pro  Asp  Glu  Pro  Ile  Ser  Asn  His  Thr  Pro  Cys  Ile  Met  Lys  Val  Asp
               100                     105                     110

Ser  Leu  Thr  Gly  Ala  Phe  Leu  Phe  Ser  Leu  Glu  Ser  Gln  Thr  Thr  Ile
          115                     120                     125

Gly  Tyr  Gly  Val  Arg  Ser  Ile  Thr  Glu  Glu  Cys  Pro  His  Ala  Ile  Phe
     130                     135                     140

Leu  Leu  Val  Ala  Gln  Leu  Val  Ile  Thr  Thr  Leu  Ile  Glu  Ile  Phe  Ile
145                     150                     155                         160

Thr  Gly  Thr  Phe  Leu  Ala  Lys  Ile  Ala  Arg  Pro  Lys  Lys  Arg  Ala  Glu
               165                     170                     175

Thr  Ile  Lys  Phe  Ser  His  Cys  Ala  Val  Ile  Thr  Lys  Gln  Asn  Gly  Lys
               180                     185                     190

Leu  Cys  Leu  Val  Ile  Gln  Val  Ala  Asn  Met  Arg  Lys  Ser  Leu  Leu  Ile
          195                     200                     205

Gln  Cys  Gln  Leu  Ser  Gly  Lys  Leu  Leu  Gln  Thr  His  Val  Thr  Lys  Glu
     210                     215                     220

Gly  Glu  Arg  Ile  Leu  Leu  Asn  Gln  Ala  Thr  Val  Lys  Phe  His  Val  Asp
225                     230                     235                         240

Ser  Ser  Ser  Glu  Ser  Pro  Phe  Leu  Ile  Leu  Pro  Met  Thr  Phe  Tyr  His
                    245                     250                     255

Val  Leu  Asp  Glu  Thr  Ser  Pro  Leu  Arg  Asp  Leu  Thr  Pro  Gln  Asn  Leu
               260                     265                     270
```

|   |   |   |   |   |   |   |   |   |   |   |   |   |   |
|---|---|---|---|---|---|---|---|---|---|---|---|---|---|
| Lys | Glu | Lys 275 | Glu | Phe | Glu | Leu | Val 280 | Val | Leu | Leu | Asn | Ala 285 | Thr | Val | Glu |
| Ser | Thr 290 | Ser | Ala | Val | Cys | Gln 295 | Ser | Arg | Thr | Ser | Tyr 300 | Ile | Pro | Glu | Glu |
| Ile 305 | Tyr | Trp | Gly | Phe | Glu 310 | Phe | Val | Pro | Val | Val 315 | Ser | Leu | Ser | Lys | Asn 320 |
| Gly | Lys | Tyr | Val | Ala 325 | Asp | Phe | Ser | Gln | Phe 330 | Glu | Gln | Ile | Arg | Lys 335 | Ser |
| Pro | Asp | Cys | Thr 340 | Phe | Tyr | Cys | Ala | Asp 345 | Ser | Glu | Lys | Gln | Gln 350 | Leu | Glu |
| Glu | Lys | Tyr 355 | Arg | Gln | Glu | Asp | Gln 360 | Arg | Glu | Arg | Glu | Leu 365 | Arg | Thr | Leu |
| Leu | Leu 370 | Gln | Gln | Ser | Asn | Val 375 | Xaa |

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: NO ( v ) FRAGMENT TYPE: N-terminal ( x i ) SEQUENCE DESCRIPTION: SEQ ID NO:5:

CGCTTTGAAT TCATGACATC AGTTGCCAAG GTCTATTA 38

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( v ) FRAGMENT TYPE: N-terminal ( x i ) SEQUENCE DESCRIPTION: SEQ ID NO:6:

CGCTTTGAAT TCTCAGACGT TACTAATGCG CACACTA 37

( 2 ) INFORMATION FOR SEQ ID NO:7:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

CAGAAGTTAA GTCGACATGA CGTCAGTTGC CAAGGTGTAT T    41

(2) INFORMATION FOR SEQ ID NO:8:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: YES (v) FRAGMENT TYPE: N-terminal (xi) SEQUENCE DESCRIPTION: SEQ ID NO:8:

CAGAAGTTAA GCGGCCGCTC AGACATTGCT GATGCGCACA CT    42